US006803220B2

(12) United States Patent
Yano et al.

(10) Patent No.: US 6,803,220 B2
(45) Date of Patent: Oct. 12, 2004

(54) POLYHYDROXYALKANOATE SYNTHASE AND GENE ENCODING THE SAME ENZYME

(75) Inventors: Tetsuya Yano, Kanagawa (JP); Takeshi Imamura, Kanagawa (JP); Sakae Suda, Kanagawa (JP); Tsutomu Honma, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/259,632

(22) Filed: Sep. 30, 2002

(65) Prior Publication Data

US 2003/0077746 A1 Apr. 24, 2003

Related U.S. Application Data

(63) Continuation-in-part of application No. 09/820,952, filed on Mar. 30, 2001, now abandoned.

(30) Foreign Application Priority Data

Mar. 30, 2000 (JP) ....................... 2000-095003

(51) Int. Cl.⁷ .......................... C12N 9/02; C12N 15/00; C12P 21/04; C12Q 1/68; C07H 21/04
(52) U.S. Cl. .................... 435/189; 435/440; 435/71.1; 435/6; 435/252.3; 435/320.1; 536/23.2
(58) Field of Search .............................. 435/189, 252.3, 435/320.1, 6, 440; 536/23.2

(56) References Cited

U.S. PATENT DOCUMENTS

| 4,393,167 A | 7/1983 | Holmes et al. | ................ | 525/64 |
| 4,477,645 A | 10/1984 | Holmes et al. | .............. | 528/361 |
| 5,135,859 A | 8/1992 | Witholt et al. | ............... | 435/135 |
| 5,200,332 A | 4/1993 | Yamane et al. | .............. | 435/135 |
| 5,292,860 A | 3/1994 | Shiotani et al. | .............. | 528/361 |
| 5,849,894 A | 12/1998 | Clemente et al. | ........... | 536/23.2 |
| 5,968,805 A | 10/1999 | Doi et al. | ................. | 435/252.3 |
| 6,485,951 B2 | 11/2002 | Yano et al. | .................. | 435/190 |
| 2001/0046692 A1 | 11/2001 | Yano et al. | .................. | 435/135 |
| 2001/0053544 A1 | 12/2001 | Yano et al. | .................. | 435/196 |
| 2001/0055795 A1 | 12/2001 | Yano et al. | .................. | 435/135 |
| 2002/0098565 A1 | 7/2002 | Yano et al. | .................. | 435/196 |
| 2003/0049806 A1 | 3/2003 | Yano et al. | .................. | 435/135 |
| 2003/0082777 A1 | 5/2003 | Yano et al. | .................. | 435/135 |
| 2003/0087413 A1 | 5/2003 | Yano et al. | .................. | 435/196 |
| 2003/0092141 A1 | 5/2003 | Yano et al. | .................. | 435/135 |
| 2003/0124692 A1 | 7/2003 | Yano et al. | .................. | 435/196 |

FOREIGN PATENT DOCUMENTS

| EP | 0 897 005 | 2/1999 |
| EP | 1 120 461 | 8/2001 |
| JP | 5-7492 | 3/1993 |
| JP | 5-93049 | 4/1993 |
| JP | 7-14352 | 1/1995 |
| JP | 7-265065 | 10/1995 |
| JP | 2642937 | 5/1997 |
| JP | 9-191893 | 7/1997 |
| WO | WO 90/12104 | 10/1990 |
| WO | WO 91/00917 | 1/1991 |
| WO | WO 01/11014 | 2/2001 |

OTHER PUBLICATIONS

H. Matsusake et al., "PHA Synthase 1" Retrieved from EBI, Database Accession No. Q9Z3Y1, May 1, 1999 (XP–002176385), Abstract.
H. Matsusake et al., "PHA Synthase 2" Retrieved from EBI, Database Accession No. Q9Z3X9, May 1, 1999 (XP–002176384), Abstract.
H. Matsusake et al., "Pseudomonas sp. 61–3 Genes for PHA Synthase 1, PHA Depolymeras , PHA Synthase 2 and PhaD, Complete CDs" Retrieved from EBI, Database Accession No. AB014758, Dec. 12, 1998 (XP–002176386), Abstract.
K. Fritzsche et al., "An Unusual Bacterial Polyester With a Phenyl Pendant Group," 191 *Makromol. Chem.* 1957–1965 (1990).
J. Marmur, "A Procedure for the Isolation of Deoxyribonucleic Acid From Micro–Organisms," 3 *J. Mol. Biol.* 208–218 (1961).
*Methods in Enzymology*, vol. 68, p. 253 (1979).
O. Peoples et al., "Poly–β–hydroxybutyrate Biosynthesis in *Alcaligenes eutrophus* H16," 264(26) *J. Biol. Chem.* 15293 (1989).
G. W. Huisman et al., "Metabolism of Poly(3–hydroxyalkanoates) (PHAs) by *Pseudomonas oleovorans*," 266 *J. Biol. Chem.* 2191 (1991).
U. Pieper et al., "Identification, Cloning and Sequence Analysis of the Poly(3–hydroxialkanoic acid) Synthase Gene of the Gram–Positive Bacterium *Rhodococcus ruber*," 96 *FEMS Micr biol. Lett.* 73 (1992).
A. Timm et al., "Cloning and Molecular Analysis of the Poly(3–hydroxyalkanoic acid) G n Locus of *Pseudomonas aeruginosa* PAO1," *Eur. J. Biochem.* 15 (1992).
H. Matsusaki et al., "Cloning and Molecular Analysis of the Poly)3–hydroxybutyrate) and Poly(3–hydroxybutyrate)–co–3–hydroxyalkanoate) Biosynthesis Genes in *Pseudomonas p.* Strain 61–3," 180(24) *J. Bacteriol.* 6459 (1998).
Matsusake et al., SPTREMBL Database—Accession BAA 36200.1–1998.

(List continued on next page.)

*Primary Examiner*—P. Achutamurthy
*Assistant Examiner*—Yong D. Pak
(74) *Attorney, Agent, or Firm*—Fitzpatrick, Cella, Harper & Scinto

(57) ABSTRACT

A novel polyhydroxyalkanoate (PHA) synthase derived from a microorganism capable of producing a PHA having a novel side-chain structure and a DNA encoding the amino acid sequence for the synthase are provided. Two PHA synthase proteins (SEQ ID NOs. 1 and 3) derived from *Pseudomonas cichorii* H45 (FERM BP-7374) and PHA synthase genes encoding these PHA synthases are provided, respectively (SEQ ID NOs. 2 and 4). A recombinant microorganism is endowed with a PHA producing ability.

4 Claims, No Drawings

OTHER PUBLICATIONS

A. Hinnen et al., "Transformation of Yeast," 75(4) *Proc. Natl. Acad. Sci.* 1929–1933 (1978).

H. Ito et al., "Transformation of Intact Yeast Cells Treated with Alkall Cations," 153(1) *J. Bacteriol.* 163–168 (1983).

Belén Garcia et al., "Novel Biodegradable Aromatic Plastics from a Bacterial Source," 274(41) *J. Biol. Chem.* 29228–28241 (1999).

D.M. Becker et al., "High–Efficiency Transformation of Yeast by Electroporation," 194 *M th ds Enzymol.* 182–187 (1990).

POLYHYDROXYALKANOATE SYNTHASE AND GENE ENCODING THE SAME ENZYME

This is a continuation-in-part application of U.S. patent application Ser. No. 09/820,952 filed on Mar. 30, 2001, now abandoned.

BACKGROUND OF THE INVENTION

1. Field of the Invention

This invention relates to a polyhydroxyalkanoate (hereinafter, referred to as a "PHA") synthase, a gene encoding the PHA synthase, a recombinant vector containing the gene, a transformant capable of expressing the PHA synthase which has been transformed by the recombinant vector, a process for producing the PHA synthase utilizing the transformant, and a process for preparing the PHA utilizing the transformant. In particular, this invention relates to a microorganism-derived PHA synthase capable of producing a polyhydroxyalkanoate and a gene encoding the PHA synthase utilized for expressing the PHA synthase by transformation.

2. Related Background Art

There have been reported a number of microorganisms producing poly-3-hydroxybutyric acid (PHB) or another PHA and storing it therein ("Biodegradable Plastic Handbook", edited by Biodegradative Plastic Research Society, NTS Co. Ltd., p.178–197). These polymers may be, as conventional plastics, used for producing a variety of products by, for example, melt-processing. Since they are biodegradable, they have an advantage that they can be completely degraded by microorganisms in the natural environment, and they do not cause pollution due to remaining in the natural environment like many conventional polymer compounds. Furthermore, they are excellently biocompatible, and thus are expected to be used in applications such as a medical soft member.

It is known that a composition and a structure of such a PHA produced by a microorganism may considerably vary depending on the type of a microorganism used for the production, a culture-medium composition and culturing conditions. Investigations have been, therefore, mainly focused on controlling such a composition or structure for the purpose of improving physical properties of a PHA.

For example, Japanese Patent Application Laid-Open Nos. 6-15604, 7-14352 and 8-19227 describe that *Alcaligenes eutropus* H16 (ATCC No. 17699) and its variants may produce 3-hydroxybutyric acid (3HB) and its copolymer with 3-hydroxyvaleric acid (3HV) with various composition ratios by changing a carbon source during culturing.

Japanese Patent Publication No. 2642937 discloses that PHA in which a monomer unit is 3-hydroxyalkanoate with 6 to 12 carbon atoms may be produced by supplying a non-cyclic aliphatic hydrocarbon as a carbon source to *Pseudomonas oleovorans* (ATCC No. 29347).

Japanese Patent Application Laid-Open No. 5-74492 discloses methods in which Methylobaterium sp., Paracoccus sp., Alcaligenes sp., and Pseudomonas sp. are contacted with a primary alcohol with 3 to 7 carbon atoms to produce a copolymer of 3HB and 3HV.

Japanese Patent Application Laid-Open Nos. 5-93049 and 7-265065 disclose that *Aeromonas caviae* is cultured using oleic acid or olive oil as a carbon source to produce a two-component copolymer of 3HB and 3-hydroxyhexanoic acid (3HHx).

Japanese Patent Application Laid-Open No. 9-191893 discloses that *Comamonas acidovorans* IFO13852 is cultured using gluconic acid and 1,4-butanediol as carbon sources to produce a polyester having 3HB and 4-hydroxybutyric acid as monomer units.

Furthermore, it is reported that certain microorganisms produce PHAs having a variety of substituents such as unsaturated hydrocarbon, ester, aryl (aromatic), and cyans groups, halogenated hydrocarbon and epoxide. Recently, there have been attempts for improving physical properties of a PHA produced by a microorganism using such a procedure. For example, Makromol. Chem., 191, 1957–1965 (1990); Macromolecules, 24, 5256–5260 (1991); and Chirality, 3, 492–494 (1991) describe production of a PHA comprising 3-hydroxy-5-phenylvaleric acid (3HPV) as a monomer unit by *Pseudomonas oleovorans*, where variations in polymer physical properties probably due to the presence of 3HPV were observed.

As described above, microorganism-produced PHAs with various combinations of composition and structure have been obtained by varying factors such as the type of a microorganism used, a culture medium composition and culturing conditions. Each microorganism has an intrinsic PHA synthase with a substrate specificity which is significantly different from others. Thus, it has been difficult to produce PHAs comprising different monomer units suitable to a variety of applications using known microorganisms or PHA synthases in such known microorganisms.

Meanwhile, as described above, a PHA having a variety of substituents in its side chains may be expected to be a "functional polymer" having significantly useful functions and properties owing to the properties of the introduced substituents. It is, therefore, extremely useful and important to search and develop a microorganism which can produce and store a very useful polymer having both such functionality and biodegradability. Furthermore, identification of a PHA synthase involved in production of the highly useful PHA and obtaining a gene encoding the PHA synthase may allow us to produce a novel transformed microorganism capable of producing a desired PHA. That is, constructing a recombinant vector comprising a gene encoding a PHA synthase and providing a microorganism transformed by the recombinant vector may allow us to prepare a PHA using the transformed microorganism or to express a recombinant type of PHA synthase. As described above, it may be important that a transformed microorganism is used to prepare a desired PHA for providing a highly useful tool for improving a productivity for the PHA and for promoting utilization of the PHA.

SUMMARY OF THE INVENTION

Objects of this invention which can solve the above problems are to search a novel microorganism capable of producing and storing in microorganisms a PHA having a novel side-chain structure, to identify an enzyme protein related to the ability of producing the novel PHA, i.e., a novel PHA synthase, and to determine a gene encoding its amino acid sequence. More specifically, an object of the present invention is to provide a novel PHA synthase derived from a microorganism producing a PHA having a novel side chain structure and a DNA encoding its amino acid sequence. Another object of this invention is to provide a recombinant vector to which a DNA encoding an available PHA synthase is introduced and which is used for transformation of a microorganism and a transformed microorganism produced using the recombinant vector. A further object of this invention is to provide a process for expressing and producing a recombinant PHA synthase in the transformed microorganism and a process for preparing a desired PHA using the transformed microorganism.

Still another object of this invention is to provide a modified PHA synthase in which its amino acid sequence is modified as long as an enzyme activity is not affected in expression of the recombinant PHA synthase in the transformed microorganism as described above and a DNA encoding the modified amino acid sequence.

For developing a PHA having a novel side-chain structure useful as, for example, a device material or a medical material aiming at solving the above problems, the inventors have searched a novel microorganism capable of producing and storing the desired PHA therein. Additionally, the inventors have intensely investigated selected novel microorganisms producing a novel PHA for identifying a PHA synthase involved in production of the novel PHA and for obtaining a gene encoding the PHA synthase. Furthermore, the inventors have conducted investigation for constructing a recombinant vector with a gene for the obtained PHA synthase, transforming a host microorganism using the recombinant vector, expressing a recombinant PHA synthase in the transformed microorganism obtained and determining production of the desired PHA.

In the course of the above investigation, the inventors synthesized 5-(4-fluorophenyl) valeric acid (FPVA) represented by formula (II):

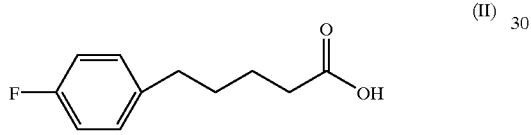

(II)

and separated from a soil a novel microorganism capable of converting the above compound (II) as a starting material (substrate) into corresponding 3-hydroxy-5-(4-fluorophenyl)valeric acid (3HFPV) represented by formula (III):

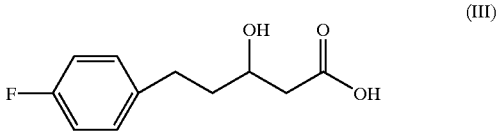

(III)

and producing and storing a novel PHA with a monomer unit represented by formula (I):

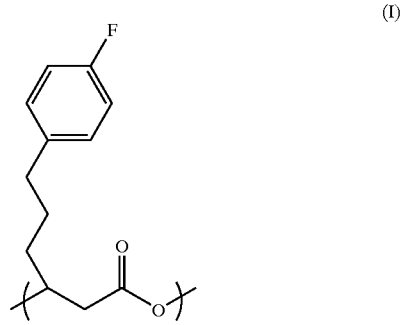

(I)

derived from 3HFPV. The novel microorganism separated is designated as H45 strain. The inventors have also found that in addition to the above enzymatic activity for converting FPVA into 3HFPV, the H45 strain may also use 4-cyclohexylbutyric acid (CHxBA) represented by formula (IV):

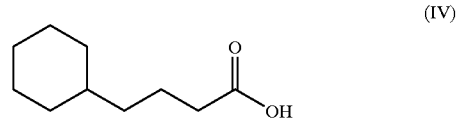

(IV)

as a starting material (substrate) to convert it into 3-hydroxy-4-cyclohexylbutyric acid (3HCHxB) represented by formula (V):

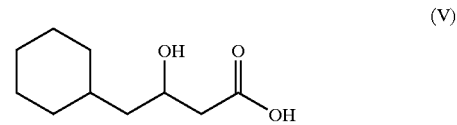

(V)

and to produce and store a PHA with a monomer unit represented by formula (VI):

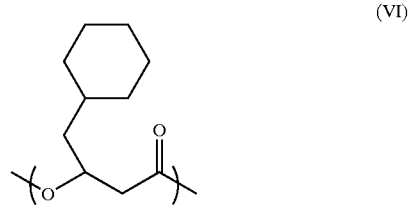

(VI)

derived from 3HCHxB.

Microbiological properties of H45 strain are as follows.

<Microbiological properties of H45 strain>

Morphologic Properties

Cell shape and size: Bacilliform, 0.8 $\mu$m×1.0 to 1.2 $\mu$m

Cell polymorphism: No

Motility: Yes

Sporulation: No

Gram stainability: Negative

Colonization: Circular, smooth in the overall periphery, low convex, smooth surface, gloss, yellowish white Physiological Properties Catalase: Positive Oxidase: Positive O/F test: oxidized form Reduction of a nitrate: Negative Indole formation: Negative Acidification of dextrose: Negative Arginine dihydrolase: Negative Urease: Negative Esculin hydrolysis: Negative Gelatin hydrolysis: Negative β-Galactosidase: Negative Fluorochrome production on King's B agar: Positive Formation with 4% Nacl: Negative Accumulation of poly-β-hydroxybutyric acid: Negative Substrate Assimilation Ability Dextrose: Positive L-Arabinose: Negative D-Mannose: Positive
D-Mannitol: Positive
N-Acetyl-D-glucosamine: Positive
Maltose: Negative
Potassium gluconate: Positive
n-Capric acid: Positive
Adipic acid: Negative
dl-Malic acid: Positive
Sodium citrate: Positive
Phenyl acetate: Positive From these microbiological properties, the inventors have attempted to categorize H45 strain according to Bergey's Manual of Systematic Bacteriology, Volume 1 (1984) and Bergey's Manual of Determinative Bacteriology 9th ed. (1994) to determine that the strain belongs to *Pseudomonas cichorii*. Thus, it was designated as *Pseudomonas cichorii* H45. There have been no reports on a strain in *Pseudomonas cichorii* capable of producing a PHA as exhibited by H45 strain. The inventors have, therefore, determined that P161 strain is a novel microorganism. The applicant deposited *Pseudomonas cichorii* H45 to Patent Microorganism Depository Center in the National Institute of Bioscience and Human Technology, Agency of Industrial Science and Technology, Ministry of International Trade and Industry, under the deposition number of FERM P-17410. H45 strain has been internationally deposited on the basis of the Budapest Treaty, and its international accession number is "FERM BP-7374".

The inventors achieved cloning a gene for a PHA synthase from the novel microorganism H45 strain and sequenced the gene. The inventors also determined an amino acid sequence for the PHA synthase encoded by the gene. Based on the above observation, the present invention was achieved.

Specifically, a PHA synthase of the present invention is a polyhydroxyalkanoate synthase having an amino acid sequence of SEQ ID NO. 1 or 3. Furthermore, the PHA synthase of the present invention may be a PHA synthase substantially retaining the amino acid sequence of SEQ ID NO. 1 and having a modified amino acid sequence where amino acids are deleted, substituted or added as long as it does not deteriorate an activity as the polyhydroxyalkanoate synthase, or a PHA synthase substantially retaining the amino acid sequence of SEQ ID NO. 3 and having a modified amino acid sequence where amino acids are deleted, substituted or added as long as it does not deteriorate activity as the polyhydroxyalkanoate synthase.

A PHA synthase gene of the present invention is a gene for a polyhydroxyalkanoate synthase comprising a DNA encoding the amino acid sequence of SEQ ID NO. 1 or the sequence of its modified amino acid, or a gene for a polyhydroxyalkanoate synthase comprising a DNA encoding the amino acid sequence of SEQ ID NO. 3 or the sequence of its modified amino acid. Embodiments of a PHA synthase gene of the present invention derived from a genome gene in H45 strain include a PHA synthase gene comprising a DNA sequence of SEQ ID NO. 2 as a DNA encoding the amino acid sequence of SEQ ID NO. 1 and a PHA synthase gene comprising a DNA sequence of SEQ ID NO. 4 as a DNA encoding the amino acid sequence of SEQ ID NO. 3.

This invention also provides a recombinant vector comprising a gene DNA encoding the above amino acid sequence as a polyhydroxyalkanoate synthase gene. This invention also provides a transformed microorganism transformed by introducing a recombinant vector adapted to a host.

The present invention also provides a process for preparing a polyhydroxyalkanoate comprising the steps of culturing the transformed microorganism to which a recombinant vector has been introduced in a culture medium containing a substrate for a polyhydroxyalkanoate synthase and collecting the polyhydroxyalkanoate from the culture preparation. The present invention also provides a process for producing a polyhydroxyalkanoate comprising the steps of culturing the transformed microorganism to which a recombinant vector has been introduced and making the transformed microorganism produce the polyhydroxyalkanoate.

A preferable process for producing a polyhydroxyalkanoate may utilize substrate specificity characteristic of a polyhydroxyalkanoate synthase derived from H45 strain: for example, preparation of a polyhydroxyalkanoate comprising a monomer unit represented by formula (I) derived from 3HFPV utilizing the above transformed microorganism or preparation of a polyhydroxyalkanoate comprising a monomer unit represented by formula (VI) derived from 3HCHxB.

A PHA synthase and a gene encoding the PHA synthase of the present invention are derived from a novel microorganism, *Pseudomonas cichorii* H45 strain and exhibits such substrate specificity that it selectively produces a PHA comprising a monomer unit having a novel side chain structure. A recombinant vector comprising the PHA synthase gene and a microorganism transformed by the recombinant vector are capable of producing a PHA exhibiting substrate specificity similar to *Pseudomonas cichorii* H45. Thus, a PHA synthase gene of this invention encodes an enzyme which permits preparation of a PHA selectively comprising a monomer unit having a novel side-chain structure and allows us to create a transformed microorganism useful for preparing a PHA having various useful physical properties which may be expected to be applied to a functional polymer.

DETAILED DESCRIPTION OF THE PREFERRED EMBODIMENTS

A PHA synthase of this invention is an enzyme protein derived from a novel microorganism isolated by the present inventors, *Pseudomonas cichorii* H45 (FERM P-17410 FERM BP-7374). Specifically, it can covert 5-(4-fluorophenyl)valeric acid (FPVA) into corresponding 3-hydroxy-5-(4-fluorophenyl)valeric acid (3HFPV) and thus has enzymatic activity involved in production of a PHA comprising a corresponding monomer unit.

A PHA synthase and a gene encoding the enzyme of this invention will be more specifically described.

From H45 strain, the inventors have cloned a gene translated into a PHA synthase which exhibits the above substrate specificity, to determine the presence of a PHA synthase comprising at least two amino acid sequences. Specifically, a PHA synthase of this invention in a chromogene in H45 strain comprises two enzymes, i.e., a PHA synthase comprising the amino acid sequence of SEQ ID NO. 1 encoded by a DNA having the sequence of SEQ ID NO. 2 and a PHA synthase comprising the amino acid sequence of SEQ ID NO. 3 encoded by a DNA having the sequence of SEQ ID NO. 4. Gene DNAs of the sequences of SEQ ID NOs. 2 and 4 may be cloned by the following procedure.

Since a PHA synthase is an enzyme protein translated from a chromogene in *Pseudomonas cichorii* H45 strain, a chromosome DNA containing a desired PHA synthase is first obtained. A chromosome DNA may be separated from H45 strain cells by a known separation method. For example, H45 strain is cultured in a LB medium or an M9 medium supplemented with an appropriate carbon source, disrupt and treated as described by, for example, Marmer et al. in Journal of Molecular Biology, Vol. 3, p. 208 (1961) to prepare a chromosome DNA.

Then, a gene library is prepared from the chromosome DNA thus obtained. The chromosome DNA is degraded using an appropriate restriction enzyme (e.g., Sau3AI) and a fragment with a proper length is ligated with a ligatable vector truncated with a restriction enzyme (e.g., BamHI) to prepare a gene library.

Depending on a vector used in preparing a library, a proper fragment length varies, e.g., about 4000 to 25000 bps for a usual plasmid vector and about 15000 to 30000 bps for a cosmid or phage vector. A proper length of DNA fragment may be collected by a known method such as a method using a sucrose density gradient or using an agarose gel described in Molecular Cloning, Cold Spring Harbor Laboratory (1982).

Since E. coli is used as a host microorganism in a gene library, a vector is a phage vector or plasmid vector which can autonomously grow in the host microorganism (E. coli). Examples of phage or cosmic vectors generally used include pWE15, M13, λEMBL3, λEMBL4, λFIXII, λDASHII, λZAPII, λgt10, λgt11, Charon4A and Charon21A. Examples of frequently used plasmid vectors include pBR, pUC, pBluescriptII, pGEM, pTZ and pET groups. In addition to E. coli, various shuttle vectors may be used, e.g., vectors which may autonomously replicate in a plurality of host microorganisms such as Pseudomonas sp. Again, these vectors may be, depending on a chromosome DNA to be ligated to them, truncated with a proper restriction enzyme to provide a desired fragment.

A chromosome DNA fragment may be ligated with a vector fragment using a DNA ligase. For example, a commercially available ligation kit (Takara Shuzo Co., Ltd., etc.) may be used. Thus, for example, various chromosome DNA fragments may be ligated with a plasmid vector fragment to prepare a mixture of recombinant plasmids comprising various DNA fragments (hereinafter, referred to as a "gene library").

In addition to a method using a proper length of chromosome DNA fragment, a gene library may be prepared by a method that all mRNAs are extracted from H45 strain, purified and used for preparation of a cDNA fragment using a reverse transcriptase as described in Molecular Cloning, Cold Spring Harbor Laboratory, 1982. Alternatively, a prepared vector is used in a gene library to transform or transduce to E. coli, and then the host E. coli is cultured to amplify the gene library to a large amount as described in Molecular Cloning, Cold Spring Harbor Laboratory, 1982.

A recombinant vector comprising a gene DNA fragment may be introduced into a host microorganism by a known method. For example, when using E. coli as a host microorganism, a recombinant plasmid vector may be introduced using a calcium chloride method (Journal of Molecular Biology, Vol. 53, p. 159 (1970)), a rubidium chloride method (Methods in Enzymology, Vol. 68, p. 253 (1979)), electroporation (Current Protocols in Molecular Biology, Vol. 1, p. 1.8.4 (1994)). When using a cosmid vector or phage vector, transduction in a host E. coli may be conducted using in vitro packaging (Current Protocols in Molecular Biology, Vol. 1, p. 5.7.1 (1994)). Alternatively, conjugational transfer with a strain retaining a recombinant vector may be utilized to prepare a strain retaining a vector.

Then, from the gene library, a probe is prepared for obtaining a DNA fragment comprising a PHA synthase gene of H45 strain.

Some base sequences have been reported for PHA synthase genes in known microorganisms; for example, Peoples, O. P. and Sinskey, A. J., J. Biol. Chem., 264, 15293 (1989); Huisman, G. W. et al., J. Biol. Chem., 266, 2191 (1991); Pieper, U. et al., FEMS Microbiol. Lett., 96, 73 (1992); Timm, A. and Steinbuchel, A., Eur. J. Biochem., 209, 15(1992); Matsusaki, H. et al., J. Bacteriol., 180, 6459 (1998). These reported sequences are compared to select a region where a sequence is preserved to a higher degree and thus to design an oligonucleotide for a primer used in polymerase chain reaction (hereinafter, referred to as "PCR"). Such oligonucleotides for a primer utilizing a common feature of PHA synthase genes include, but not limited to, a sequence described in Timm, A. and Steinbuchel, A., Eur. J. Biochem., 209, 15 (1992). An oligonucleotide may be synthesized using, for example, a commercially available DNA synthesizer such as Custom Synthesis Service, Amersham-Pharmacia Biotech, depending on a designed sequence.

For a PHA synthase gene derived from H45 of this invention, synthetic DNAs having the sequences of SEQ ID NOs. 5 and 6 were designed.

Then, the designed oligonucleotide as a primer is subject to polymerase chain reaction (PCR) using a chromosome DNA in H45 strain as a template to obtain a PCR amplified fragment. The PCR amplified fragment, which is derived from the primer, comprises a sequence common in PHA synthase genes at both ends. A partial sequence derived from the PHA synthase gene itself in H45 strain as a template is contained between sequences complementary to the primer at both ends.

The PCR amplified fragment obtained is, therefore, almost 100% homologous to the PHA synthase gene in H45 strain and is expected to exhibit a higher S/N ratio as a probe in colony hybridization. In addition, it may facilitate stringency control of hybridization.

The above PCR amplified fragment is labeled with an appropriate reagent and used as a probe to colony-hybridize the above chromosome DNA library for selecting a recombinant E. coli strain retaining the PHA synthase gene (Current Protocols in Molecular Biology, Vol. 1, p. 6.0.3 (1994)). For example, the PCR amplified fragment may be labeled using a common detection system using a labeled enzyme or a commercially available kit such as AlkPhos-Direct (Amersham-Pharmacia Biotech).

A recombinant E. coli strain retaining a gene fragment comprising a PHA synthase gene may be selected by, in addition to the above method using a gene type, a method using a phenotype where PHA synthesis is directly evaluated. Specifically, in expression of a PHA synthase from a retained PHA synthase gene in a recombinant E. coli strain, PHA is produced by the PHA synthase. PHA synthesis may be detected to select a recombinant E. coli strain in which the PHA synthase is expressed. PHA synthesis may be detected by, for example, staining with Sudan Black B (Archives of Biotechnology, Vol. 71, p. 283 (1970)) or determination of PHA accumulation by phase contrast microscopy.

A plasmid is collected from a recombinant E. coli selected by any of the above methods using an alkali method (Current Protocols in Molecular Biology, Vol. 1, p. 1.6.1 (1994)). The collected plasmid may be used to provide a DNA fragment comprising a PHA synthase gene or multiple DNA fragments partially containing a PHA synthase gene. The DNA fragment obtained may be sequenced by, for example, the Sanger's sequencing method (Molecular Cloning, Vol. 2, p. 13.3 (1989). Specifically, it may be conducted by a dyeprimer method or a dye-terminator method using an automatic sequencer such as DNA Sequencer 377A (Parkin Elmer). Since the sequence of the vector itself in which the DNA fragment has been incorporated is known, the sequence of the DNA fragment cloned therein may be unequivocally analyzed.

After sequencing all the obtained DNA fragments comprising a PHA synthase gene, hybridization may be conducted using a DNA fragment prepared by an appropriate method such as chemical synthesis, PCR using a chromosome DNA as a template or degradation of a DNA fragment comprising the sequence with a restriction enzyme as a probe to provide a PHA synthase gene DNA of this invention.

The inventors have selected a gene translated into a PHA synthase exhibiting the above substrate specificity from H45 strain according to the above procedure to find a PHA synthase comprising at least two amino acid sequences. Specifically, the inventors have found a PHA synthase gene collected from the chromosome DNA of H45 strain and comprising the sequence of SEQ ID NO. 2 and a PHA synthase encoded by the gene and comprising the amino acid of SEQ ID NO. 1 as well as a PHA synthase gene comprising the sequence of SEQ ID NO. 4 and a PHA synthase encoded by the gene and comprising the amino acid of SEQ ID NO. 3.

A PHA synthase gene of the present invention may include a degenerated isomer encoding the same polypeptide which has the same amino acid sequence and is different in a degeneration codon. More specifically, it also includes a degenerated isomer by selection and conversion of a more frequently used degenerated codon encoding the same amino acid depending on a host. Besides the PHA synthase comprising the amino acid sequence of SEQ ID NO. 1 inherent in H45 strain and the PHA synthase comprising the amino acid sequence of SEQ ID NO. 3, a PHA synthase of this invention may have mutation such as deletion, substitution and addition for several amino acids as long as its PHA producing activity and substrate specificity may not be deteriorated or the amino acid sequence may be maintained. Mutation such as deletion, substitution and addition may be introduced by a site mutation introduction technique based on a PHA synthase gene inherent in H45 strain having the sequence of SEQ ID NO. 2 or 4 (Current Protocols in Molecular Biology Vol. 1, p. 8.1.1 (1994)).

A recombinant vector of the present invention is used in an application where a recombinant PHA synthase of this invention is expressed using Pseudomonas sp. or a microorganism such as E. coli as a host. It is, therefore, preferable that the recombinant vector of this invention itself can autonomously replicate in a host used while comprising a promoter for expression, a PHA synthase gene DNA of this invention and a transcription termination sequence suitable to the host. In addition, it is preferable that after introducing the recombinant vector, a vector comprising various marker genes used for its selection is used.

Expression vectors suitable to various types of bacterial hosts such as Pseudomonas sp. and E. coli include pLA2917 (ATCC 37355) having a RK2 replication origin which may be replicated and retained by a range of hosts or pJRD215 (ATCC 37533) having a RSF1010 replication origin. Without being limited to these, any vector having a replication origin which may be replicated and retained by a range of hosts may be used. Any promoter which may be expressed in a bacterium as a host may be used; for example, promoters derived from E. coli, a phage, etc. such as trp, trc, tac, lac, PL, PR, T7 and T3 promoters.

When using a yeast as a host, an expression vector may be YEp13, YCp50, pRS or pYEX vector. A promoter may be, for example, GAL or A0D promoter.

A transformed microorganism of this invention may be produced by introducing a recombinant vector of this invention into a host suitable to an expression vector used during preparing the recombinant vector. Examples of bacteria which may be used as a host include Esherichia sp., Pseudomonas sp., Ralstonia sp., Alcaligenes sp., Comamonas sp., Burkholderia sp., Agrobacterium sp., Flabobacterium sp., Vibrio sp., Enterobacter sp., Rhizobium sp., Gluconobacter sp., Acinetobacter sp., Moraxella sp., Nitrosomonas sp., Aeromonas sp., Paracoccus sp., Bacillus sp., Clostridium sp., Lactobacillus sp., Corynebacterium sp., Arthrobacter sp., Achromobacter sp., Micrococcus sp., Mycobacterium sp., Streptococcus sp., Streptomyces sp., Actinomyces sp., Norcadia sp. and Methylobacterium sp. A recombinant DNA may be introduced into a bacterium by an appropriate technique such as the above calcium chloride method and electroporation.

Besides the above bacteria, yeasts and molds such as Saccharomyces sp. and Candida sp. may be used as a host. A recombinant DNA may be introduced into an yeast by, for example, electroporation (Methods Enzymol., 194, 182–187 (1990)), a spheroplast method (Proc. Natl. Acad. Sci. USA, 84, 1929–1933 (1978)) and a lithium acetate method (J. Bacteriol., 153, 163–168 (1983)).

A PHA synthase of this invention may be prepared by culturing a transformant of this invention prepared by the above procedure and making a corresponding PHA synthase gene in an introduced expression vector producing the synthase as a recombinant protein. The PHA synthase of this invention is produced and accumulated in the culture (cultured bacterium or culture supernatant) and separated from the culture to be used for production of a recombinant enzyme protein. For this purpose, a transformant of this invention may be cultured by a usual procedure used for culturing a host. Culturing may be conducted by any of common methods used for culturing a microorganism such as batch, flow batch, continuous culturing and reactor styles. This culturing may be conducted by using, for example, a medium containing an inducer for expressing the above polyhydroxyalkanoate synthase gene.

For a transformant obtained using a bacterium such as E. coli as a host, a medium used for culturing may be a complete medium or synthetic medium such as LB medium and M9 medium. A microorganism may be grown by aerobically culturing at a culturing temperature of 25 to 37° C. for 8 to 72 hours. Then, the bacteria are collected for obtaining a PHA synthase accumulated in them. Examples of a carbon source for the microorganism include sugars such as glucose, fructose, sucrose, maltose, galactose and starches; lower alcohols such as ethanol, propanol and butanol; polyalcohols such as glycerol; organic acids such as acetic acid, citric acid, succinic acid, tartaric acid, lactic acid and gluconic acid; and aliphatic acids such as propionic acid, butanoic acid, pentanoic acid, hexanoic acid, heptanoic acid, octanoic acid, nonanoic acid, decanoic acid, undecanoic acid and dodecanoic acid.

Examples of a nitrogen source include ammonia; ammonium salts such as ammonium chloride, ammonium sulfate and ammonium phosphate; and natural product derivatives such as peptone, meat extract, yeast extract, malt extract, casein decomposition products and corn steep liquor. Examples of an inorganic material include potassium dihydrogen phosphate, potassium monohydrogen phosphate, magnesium phosphate, magnesium sulfate and sodium chloride. The culture medium may contain an antibiotic such as kanamycin, ampicillin, tetracyclin, chloramphenicol and streptomycin, depending on, for example, the type of a drug resistance gene used as a marker gene.

When using an inducible promoter in an expression vector, expression may be enhanced by adding a proper inducer depending on the type of the promoter during culturing a transformed microorganism. For example, the inducer may be isopropyl-β-D-thiogalactopyranoside (IPTG), tetracyclin or indoleacrylic acid (IAA).

A PHA synthase may be separated and purified by centrifuging and collecting a culture obtained and processing it by a technique such as affinity chromatography, cation or anion exchange chromatography and gel filtration alone or in combination as appropriate. Whether a purified material is a desired enzyme is determined by a usual method such as SDS polyacrylamide gel electrophoresis and Western blotting.

This invention is not limited to the procedures as described above for culturing of a transformed microorganism of the present invention, production of a PHA synthase by the transformed microorganism of this invention and accumulating it in bacterial cells, and collection and purification of the PHA synthase from the cells.

A transformed microorganism of the present invention may be used for expressing a recombinant PHA synthase to produce a desired PHA by culturing thereof. For example, the microorganism may be cultured under the above culturing conditions to produce a recombinant PHA synthase while a substrate corresponding to the desired PHA on which the PHA synthase acts is added to a medium. Most conveniently, the PHA may be collected from the culture and the producing bacteria by extraction with an organic solvent commonly used such as chloroform. In an environment where using an organic solvent such as chloroform is undesirable, the culture may be treated a surfactant such as SDS, an enzyme such as lysozyme, or an agent such as EDTA, sodium hypochlorite and ammonia to remove bacterium components other than the PHA for collecting the PHA. This invention is not limited to the above procedures for culturing of a transformed microorganism of this invention for production of a PHA, production of a PHA by and accumulation thereof in a cultured microorganism, and collection of the PHA from a recombinant microorganism.

EXAMPLES

This invention will be more specifically described with reference to Examples, although these Examples are illustrated as the best embodiments of this invention and do not limit the technical range of this invention.

Example 1

Cloning of a PHA Synthase Gene of H45 Strain

H45 strain was cultured in 100 mL of LB medium (1% polypeptone, 0.5% yeast extract, 0.5% sodium chloride, pH 7.4) at 30° C. overnight and then a chromosome DNA was separated and collected as described by Marmer. The obtained chromosome DNA was completely digested using a restriction enzyme BglII. A vector pUC18 was cleaved with a restriction enzyme BamHI. After dephosphorylation of the terminals (Molecular Cloning, Vol. 1, p. 5.7.2 (1989), Cold Spring Harbor Laboratory), the cleaved site of the vector (cloning site) and the chromosome DNA fragment after BglII complete digestion were ligated using a DNA ligation kit Ver. II (Takara Shuzo Co., Ltd.). The plasmid vector in which the chromosome DNA fragment was integrated was used to transform Escheichia coli HB101 for preparing a chromosome DNA library for H45 strain.

Then, in order to select a DNA fragment comprising a PHA synthase gene of H45 strain, a probe for colony hybridization was prepared. An oligonucleotide consisting of the sequences of SEQ ID NOs. 5 and 6 (Amersham-Pharmacia Biotech) was prepared and used as a primer for PCR using the chromosome DNA as a template. A PCR-amplified DNA fragment was used as a probe. Labeling of the probe was conducted using a commercially available labeling enzyme system AlkPhosDirect (Amersham-Pharmacia Biotech). The labeled probe thus obtained was used to select an *E. coli* strain containing a recombinant plasmid comprising the PHA synthase gene from the chromosome DNA library of H45 strain by colony hybridization. From the selected strain, the plasmid was collected by an alkali method to prepare a DNA fragment comprising a PHA synthase gene.

The gene DNA fragment thus obtained was recombined in a vector pBBR122 (Mo BiTec) comprising a wide host range of replication region which did not belong to IncP, IncQ or IncW in an incompatible group. The recombinant plasmid was transformed in *Pseudomonas cichorii* H45 ml strain (a strain depleted of PHA synthesizing ability) by electroporation, and then the H45 ml strain regained PHA synthesizing ability and exhibited complementarity. It demonstrates that the selected gene DNA fragment comprises a region of a PHA synthase gene translatable into a PHA synthase in *Pseudomonas cichorii* H45 ml.

The DNA fragment comprising a PHA synthase gene was sequenced by the Sanger's sequencing method. It was thus found that the determined sequence comprised the sequences of SEQ ID NOs. 2 and 4 each of which encoded a peptide chain. As described below, it was determined that both proteins consisting of a peptide chain had enzyme activity and that the sequences of SEQ ID NOs. 2 and 4 were therefore PHA synthase genes. Specifically, it was found that the sequences of SEQ ID NOs. 2 and 4 encoded the amino acid sequences of SEQ ID NOs. 1 and 3, respectively, and that a protein comprising one of these amino acid sequences alone could produce a PHA.

Example 2

Recombination of a PHA Synthase Gene of H45 Strain to an Expression Vector

A PHA synthase gene having the sequence of SEQ ID NO. 2 was PCRed using a chromosome DNA as a template to reproduce the whole length of a PHA synthase gene. An oligonucleotide having a sequence which was an upstream primer to the sequence of SEQ ID NO. 2 and had a sequence upstream of its initiation codon (SEQ ID NO. 7) and an oligonucleotide having a sequence which was a downstream primer to the sequence of SEQ ID NO. 2 and had a sequence downstream of its termination codon (SEQ ID NO. 8) were designed and prepared (Amersham-Pharmacia Biotech). Using these oligonucleotides as a primer, PCR was conducted to amplify the whole length of the PHA synthase gene (LA-PCR kit; Takara Shuzo Co., Ltd.).

Likewise, a PHA synthase gene having the sequence of SEQ ID NO. 4 was PCRed using a chromosome DNA as a template to reproduce the whole length of a PHA synthase gene. An oligonucleotide having a sequence which was an upstream primer to the sequence of SEQ ID NO. 4 and had a sequence upstream of its initiation codon (SEQ ID NO. 9) and an oligonucleotide having a sequence which was a downstream primer to the sequence of SEQ ID NO. 4 and had a sequence downstream of its termination codon (SEQ ID NO. 10) were designed and prepared (Amersham-Pharmacia Biotech). Using these oligonucleotides as a primer, PCR was conducted to amplify the whole length of the PHA synthase gene (LA-PCR kit; Takara Shuzo Co., Ltd.).

Each of the obtained PCR amplified fragment containing the whole length of the PHA synthase gene was completely digested using a restriction enzyme HindIII. Separately, an expression vector pTrc99A was also truncated with a restriction enzyme HindIII and dephosphorylated (Molecular Cloning, Vol. 1, p. 5.7.2 (1989), Cold Spring Harbor Laboratory). To the truncated site of the expression vector pTrc99A was ligated the DNA fragment comprising the whole length of the PHA synthase gene from which unnecessary sequences had been removed at both ends, using a DNA ligation kit Ver. II (Takara Shuzo Co., Ltd.).

Using the recombinant plasmids obtained, *Escherichia coli* HB101 (Takara Shuzo Co., Ltd.) was transformed by a calcium chloride method. The recombinants obtained were cultured, and the recombinant plasmids were amplified and collected individually. The recombinant plasmid retaining the gene DNA of SEQ ID NO. 2 was designated pH 45-C1 (derived from SEQ ID NO. 2) while the recombinant plasmid retaining the gene DNA of SEQ ID NO. 4 was designated pH 45-C2 (derived from SEQ ID NO. 4). (Example 3) PHA Production (1) using a PHA synthase gene recombinant *E. coli*.

Using the recombinant plasmids obtained in Example 2, pH 45-C1 (derived from SEQ ID NO. 2) and pH 45-C2 (derived from SEQ ID NO. 4), an *Escherichia coli* HB101fB (fadB deficient strain) was transformed by a calcium chloride method to prepare recombinant *E. coli* strains retaining the recombinant plasmid, pH 45-C1 and pH 45-C2 recombinant strains, respectively.

Each of the pH 45-C1 and pH 45-C2 recombinant strains was inoculated to 200 mL of M9 medium containing 0.5% yeast extract and 0.1% FPVA, and the medium was shaken at 37° C. with a rate of 125 strokes/min. After 24 hours, the cells were collected by centrifugation, washed once with cold methanol and lyophilized.

The lyophilized pellet was suspended in 100 mL of chloroform and the suspension was stirred at 60° C. for 20 hours to extract a PHA. After filtering the extract through a membrane filter with a pore size of 0.45 μm, the filtrate was concentrated by rotary evaporation. Then, the concentrate was re-suspended in cold methanol and the precipitant was collected and dried in vacuo to provide a PHA. The PHA thus obtained was subject to methanolysis as usual and analyzed using a gas chromatography-mass spectrometry apparatus (GC-MS, Shimadzu QP-5050, EI technique) to identify methyl-esterified PHA monomer units. Table 1 shows together a cell dry weight, a polymer dry weight for a collected PHA, a polymer yield per a cell (polymer dry weight/cell dry weight) and identities of monomer units for each strain.

TABLE 1

| | pH45-C1 recombinant strain | pH45-C2 recombinant strain |
|---|---|---|
| Cell dry weight | 730 mg/L | 770 mg/L |
| Polymer dry weight | 36 mg/L | 39 mg/L |

TABLE 1-continued

| | pH45-C1 recombinant strain | pH45-C2 recombinant strain |
|---|---|---|
| Polymer dry weight/Cell dry weight | 5% | 5% |
| Monomer unit composition (area ratio) | | |
| 3-Hydroxybutyric acid | 0% | 0% |
| 3-Hydroxyvaleric acid | 0% | 0% |
| 3-Hydroxyhexanoic acid | 0% | 0% |
| 3-Hydroxyheptanoic acid | 1% | 1% |
| 3-Hydroxyoctanoic acid | 2% | 3% |
| 3-Hydroxynonanoic acid | 0% | 1% |
| 3-Hydroxydecanoic acid | 4% | 5% |
| 3-Hydroxy-5-(4-fluorophenyl) valeric acid | 93% | 90% |

These results show that both pH 45-C1 and pH 45-C2 recombinant strains produce, from the substrate 5-(4-fluorophenyl) valeric acid, PHAs comprising a monomer unit represented by formula (I) derived from corresponding 3-hydroxy-5-(4-fluorophenyl) valeric acid as a main component. It is, therefore, demonstrated that although the pH 45-C1 and pH 45-C2 recombinant strains exclusively produce PHA synthases having the amino acid sequences of SEQ ID NOs. 1 and 3 translated from the PHA synthase genes comprising the sequences of SEQ ID NOs. 2 and 4, respectively, both strains similarly convert the substrate 5-(4-fluorophenyl) valeric acid into the monomer unit represented by formula (I) derived from corresponding 3-hydroxy-5-(4-fluorophenyl) valeric acid and produce a PHA containing the monomer unit.

Example 3

Homology of a PHAsynthase Gene of H45 Strain

In the same manner as in Example 1, the chromosome DNA of H45 strain was separated and collected. Further, *Pseudomonas olevorans* ATCC29347, *Pseudomonas putida* Tk2440 and *Pseudomonas aeruginose* PA01 were cultured and the chromosome DNAs thereof were separated and collected in the same as in Example 1.

Next, a probe for hybridization was prepared for confirming homology of a PHAsynthase gene of H45 strain. In the same manner as in Example 2, an oligonucleotide having the sequences of SEQ ID NOs 7 and 8 were synthesized. (Amersham-Pharmacia Biotech) PCR was conducted using the thus synthesized oligonucleotide as a primer and the chromosome DNA as a template. The obtained PCR amplified DNA fragments were used as a probe. Labeling of the probe using AlkphosDirect (Amersham-Pharmacia Biotech) was conducted to obtain the labeled probe referred to as "phaC1". In the same manner as above, an oligonucleotide having the sequences of SEQ ID NOs 9 and 10 were synthesized. (Amersham-Pharmacia Biotech) PCR was conducted using the thus synthesized oligonucleotide as a primer and the chromosome DNA as a template. Labeling of the obtained PCR amplified DNA fragments was conducted in the same manner as above to obtain the labeled probe referred to as "phaC2".

Using the thus obtained probes, homology of the PHA synthase gene was confirmed by a dot-blot method. The thus prepared chromosome DNA was alkalized and then blotted on a nylon film (Tropilon-45, produced by Tropix Co.) by 1 μg at respective points using a dot-blot apparatus (BRL).

The film was dried at 80° C. for two hours, then put in a vinyl bag. 3 ml of the solution for hybridization prepared according to the recipe of AlkPhosDirect was added thereto, and hybridization was conducted at 55° C. for one hour. 15 ng of the labeled probe phaC1 or phaC2 per 3 ml of the above hybridization solution (5 ng/ml) was added to the nylon film, and hybridization was conducted at 55° C. for 12 hours. And then the nylon film was put out from the vinyl bag, and washed two times for 10 minutes at 55° C. with a first washing buffer according the recipe of AlkPhosDirect. And then after it was washed two times for 5 minutes at room temperature with a second washing buffer according to the recipe of AlkPhosDirect, a detecting step was carried out using CDP-Star attached to AlkPhosDirect according to the recipe.

Further, a detecting step was carried out under the same conditions as above except that hybridization and first washing were conducted at 60° C. or 65° C. The results were shown in Table 2.

TABLE 2

| Temperature (° C.) | 55 | 60 | 65 |
|---|---|---|---|
| Probe phaC1 Target DNA | | | |
| H45 Strain | A | A | B |
| ATCC29347 Strain | C | D | D |
| KT2440 Strain | C | D | D |
| PAO1 Strain | D | D | D |
| Probe phaC2 Target DNA | | | |
| H45 Strain | A | A | B |
| ATCC29347 Strain | C | D | D |
| KT2440 Strain | C | D | D |
| PAO1 Strain | D | D | D |

A: Strong Signal,
B: Signal,
C: Slight Signal,
D: No Signal

What is claimed is:

1. An isolated polyhydroxyalkanoate synthase having the amino acid sequence of SEQ ID NO: 1.

2. An isolated polyhydroxyalkanoate synthase having an amino acid sequence, which is at least 95% homologous with the amino acid sequence of SEQ ID NO: 1.

3. A method of preparing a polyhydroxyalkanoate synthase of claim 1 or 2, comprising the steps of culturing a transformed microorganism harboring a recombinant vector containing a DNA sequence encoding said polyhydroxyalkanoate synthase in a medium; expressing said DNA; and isolating the polyhydroxyalkanoate synthase from the culture obtained.

4. A method for producing the polyhydroxyalkanoate synthase according to claim 3, wherein the DNA has the sequence according to SEQ ID NO: 2.

* * * * *

UNITED STATES PATENT AND TRADEMARK OFFICE
CERTIFICATE OF CORRECTION

PATENT NO.    : 6,803,220 B2
DATED         : October 12, 2004
INVENTOR(S)   : Tetsuya Yano et al.

It is certified that error appears in the above-identified patent and that said Letters Patent is hereby corrected as shown below:

Title page,
Item [*] Notice, insert -- This patent is subject to a terminal disclaimer. --.
Item [56], References Cited, FOREIGN PATENT DOCUMENTS, insert
-- JP  6-15604  01/1994 --.

Signed and Sealed this

First Day of March, 2005

JON W. DUDAS
*Director of the United States Patent and Trademark Office*

SEQUENCE LISTING

<160> NUMBER OF SEQ ID NOS: 10

<210> SEQ ID NO 1
<211> LENGTH: 559
<212> TYPE: PRT
<213> ORGANISM: Pseudomonas cichorii H45 ; FERM BP-7374

<400> SEQUENCE: 1

```
Met Ser Asn Lys Asn Asn Asp Asp Leu Lys Asn Gln Ala Ser Glu Asn
 1               5                  10                  15

Thr Leu Gly Leu Asn Pro Val Val Gly Leu Arg Gly Lys Asp Leu Leu
            20                  25                  30

Ala Ser Ala Arg Met Val Leu Arg Gln Ala Ile Lys Gln Pro Ile His
        35                  40                  45

Ser Ala Arg His Val Ala His Phe Gly Leu Glu Leu Lys Asn Val Leu
    50                  55                  60

Leu Gly Lys Ser Glu Leu Leu Pro Thr Ser Asp Asp Arg Arg Phe Ala
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Gly Asp Ser Asn
            100                 105                 110

Leu Pro Pro Lys Asp Val Ser Arg Gly His Phe Val Ile Asn Leu Met
        115                 120                 125

Thr Glu Ala Phe Ala Pro Thr Asn Thr Ala Ala Asn Pro Ala Ala Val
    130                 135                 140

Lys Arg Phe Phe Glu Thr Gly Gly Lys Ser Leu Leu Asp Gly Leu Ser
```

-continued

```
             145                 150                 155                 160
        His Leu Ala Lys Asp Leu Val His Asn Gly Gly Met Pro Ser Gln Val
                         165                 170                 175
        Asn Met Gly Ala Phe Glu Val Gly Lys Thr Leu Gly Val Thr Glu Gly
                         180                 185                 190
        Ala Val Val Phe Arg Asn Asp Val Leu Glu Leu Ile Gln Tyr Lys Pro
                         195                 200                 205
        Ile Thr Glu Gln Val His Glu Arg Pro Leu Leu Val Val Pro Pro Gln
                 210                 215                 220
        Ile Asn Lys Phe Tyr Val Phe Asp Leu Ser Pro Glu Lys Ser Leu Ala
        225                 230                 235                 240
        Arg Phe Cys Leu Arg Asn Asn Val Gln Thr Phe Ile Val Ser Trp Arg
                         245                 250                 255
        Asn Pro Thr Lys Glu Gln Arg Glu Trp Gly Leu Ser Thr Tyr Ile Glu
                         260                 265                 270
        Ala Leu Lys Glu Ala Val Asp Val Thr Ala Ile Thr Gly Ser Lys
                         275                 280                 285
        Asp Val Asn Met Leu Gly Ala Cys Ser Gly Gly Ile Thr Cys Thr Ala
                 290                 295                 300
        Leu Leu Gly His Tyr Ala Ala Ile Gly Glu Asn Lys Val Asn Ala Leu
        305                 310                 315                 320
        Thr Leu Leu Val Ser Val Leu Asp Thr Thr Leu Asp Ser Asp Val Ala
                         325                 330                 335
        Leu Phe Val Asp Glu Gln Thr Leu Glu Ala Ala Lys Arg Gln Ser Tyr
                         340                 345                 350
        Gln Ala Gly Val Leu Glu Gly Arg Asp Met Ala Lys Val Phe Ala Trp
                         355                 360                 365
        Met Arg Pro Asn Asp Leu Ile Trp Asn Tyr Trp Val Asn Asn Tyr Leu
                 370                 375                 380
        Leu Gly Asn Glu Pro Pro Val Phe Asp Ile Leu Phe Trp Asn Asn Asp
        385                 390                 395                 400
        Thr Thr Arg Leu Pro Ala Ala Phe His Gly Asp Leu Ile Glu Met Phe
                         405                 410                 415
        Lys Ser Asn Pro Leu Thr Arg Ala Asp Ala Leu Glu Val Cys Gly Thr
                         420                 425                 430
        Pro Ile Asp Leu Lys Lys Val Thr Ala Asp Ile Phe Ser Leu Ala Gly
                 435                 440                 445
        Thr Ser Asp His Ile Thr Pro Trp Arg Ser Cys Tyr Lys Ser Ala Gln
                         450                 455                 460
        Leu Phe Gly Gly Asn Val Glu Phe Val Leu Ser Ser Ser Gly His Ile
        465                 470                 475                 480
        Gln Ser Ile Leu Asn Pro Gly Asn Pro Lys Ser Arg Tyr Met Thr
                         485                 490                 495
        Ser Thr Gln Met Pro Ala Asp Ala Asp Trp Gln Glu Ser Thr
                         500                 505                 510
        Lys His Ala Asp Ser Trp Trp Leu His Trp Gln Ala Trp Gln Ala Gln
                         515                 520                 525
        Arg Ser Gly Asn Leu Lys Lys Ala Pro Ala Lys Leu Gly Asn Lys Ala
                 530                 535                 540
        Tyr Pro Ala Gly Glu Ala Ala Pro Gly Thr Tyr Val His Glu Arg
        545                 550                 555

<210> SEQ ID NO 2
```

-continued

<211> LENGTH: 1680
<212> TYPE: DNA
<213> ORGANISM: Pseudomonas cichorii H45 ; FERM BP-7374

<400> SEQUENCE: 2

| | | |
|---|---|---|
| atgagtaaca agaataacga tgacttgaag aatcaagcct cggaaaacac | 50 |
| cttgggctg aatcctgtcg ttggactgcg tggaaaggat ctactggctt | 100 |
| ctgctcgcat ggtactcagg caggccatca acaaccgat tcacagcgcc | 150 |
| aggcatgttg cgcatttcgg ccttgaactc aagaacgtgc tgctcggcaa | 200 |
| atccgagctg ctaccgacca gcgatgaccg tcgcttcgcg gatccggcct | 250 |
| ggagccagaa cccgctctac aaacgttatc tgcaaaccta cctggcgtgg | 300 |
| cgcaaggaac tccacgactg gatcggcgac agcaacctgc cgcccaagga | 350 |
| cgtcagccgc gggcatttcg tgatcaacct catgaccgaa gccttcgccc | 400 |
| cgaccaacac ggcggccaac ccggcggcgg tcaagcgctt cttcgaaacc | 450 |
| ggtggcaaaa gcctgctcga tggcctctcg catctggcca aggacctggt | 500 |
| gcataacggc ggcatgccga gccaggtcaa catgggcgca ttcgaggtcg | 550 |
| gcaagaccct tggtgtgacc gagggcgcag tggtctttcg caacgacgtg | 600 |
| ctggagctga tccagtacaa gccgatcacc gagcaggtgc atgaacgccc | 650 |
| actgctggtg gtaccgccgc agatcaacaa gttctacgtt ttcgacctga | 700 |
| gcccggaaaa aagcctggcg cggttctgcc tgcgcaacaa cgtgcagacc | 750 |
| ttcatcgtca gctggcgcaa cccgaccaag gagcagcgcg agtggggcct | 800 |
| gtcgacctac atcgaagcgc tcaaggaagc ggttgatgtg gtcaccgcca | 850 |
| ttaccggcag caaagacgtg aacatgctcg gtgcctgctc cggcggcatc | 900 |
| acctgcaccg cgctgctggg ccactacgca gcaatcggcg agaacaaggt | 950 |
| caacgccctg accctgctgg tcagcgtgct cgacaccacc ctggacagcg | 1000 |
| acgtggccct gttcgtcgac gagcagaccc tcgaagccgc caagcgccaa | 1050 |
| tcgtaccagg ccggcgtgct ggaaggccgc gacatggcca aggtcttcgc | 1100 |
| ctggatgcgc cccaacgacc tgatctggaa ctactgggtc aacaactacc | 1150 |
| tgttgggcaa cgaaccgccg gttttcgaca ttctgttctg gaacaacgac | 1200 |
| accacccggt tgcctgcggc gttccatggc gacctgatcg aaatgttcaa | 1250 |
| aagcaatcca ttgacccgcg ccgatgcact ggaagtgtgc ggcacgccga | 1300 |
| tcgacctgaa gaaggttacc gccgacatct tctcgctggc cggcaccagc | 1350 |
| gaccacatca cgccgtggcg ctcctgctac aagtcggcgc aactgttcgg | 1400 |
| cggcaacgtt gaattcgtgc tgtccagcag cgggcacatc cagagcattc | 1450 |
| tgaacccgcc gggcaatccg aaatcgcgct acatgaccag cacccaaatg | 1500 |
| cccgccgatg ccgatgactg gcaggaagag tcgaccaagc acgccgactc | 1550 |
| ctggtggctg cactgcaggg catggcaggc acagcgttcg gcaacctga | 1600 |
| aaaaagcacc ggcaaaactg gcaacaagg cctacccggc aggggaagcc | 1650 |
| gcaccgggca cttacgtgca tgagcggtaa | 1680 |

<210> SEQ ID NO 3
<211> LENGTH: 560
<212> TYPE: PRT
<213> ORGANISM: Pseudomonas cichorii H45 ; FERM BP-7374

<400> SEQUENCE: 3

```
Met Arg Glu Lys Pro Ala Arg Asp Ser Leu Pro Thr Pro Ala Ala Phe
 1               5                  10                  15

Ile Asn Ala Gln Ser Ala Ile Thr Gly Leu Arg Gly Arg Asp Leu Leu
            20                  25                  30

Ser Thr Leu Arg Ser Val Ala Ala His Gly Leu Arg Asn Pro Val His
        35                  40                  45

Ser Ala Arg His Ala Leu Lys Leu Gly Gly Gln Leu Gly Arg Val Leu
    50                  55                  60

Leu Gly Glu Thr Leu His Pro Thr Asn Pro Gln Asp Thr Arg Phe Ala
65                  70                  75                  80

Asp Pro Ala Trp Ser Leu Asn Pro Phe Tyr Arg Arg Ser Leu Gln Ala
                85                  90                  95

Tyr Leu Ser Trp Gln Lys Gln Val Lys Ser Trp Ile Asp Glu Ser Asp
            100                 105                 110

Met Ser Pro Asp Asp Arg Ala Arg Ala His Phe Ala Phe Ala Leu Leu
        115                 120                 125

Asn Asp Ala Val Ser Pro Ser Asn Thr Leu Leu Asn Pro Leu Ala Val
    130                 135                 140

Lys Glu Leu Phe Asn Ser Gly Gly Asn Ser Leu Val Arg Gly Ile Gly
145                 150                 155                 160

His Leu Val Asp Asp Leu Leu His Asn Asp Gly Leu Pro Arg Gln Val
                165                 170                 175

Thr Lys Gln Ala Phe Glu Val Gly Lys Thr Val Ala Thr Thr Thr Gly
            180                 185                 190

Ala Val Val Phe Arg Asn Glu Leu Leu Glu Leu Ile Gln Tyr Lys Pro
        195                 200                 205

Met Ser Glu Lys Gln Tyr Ser Lys Pro Leu Leu Val Val Pro Pro Gln
    210                 215                 220

Ile Asn Lys Tyr Tyr Ile Phe Asp Leu Ser Pro His Asn Ser Phe Val
225                 230                 235                 240

Gln Tyr Ala Leu Lys Asn Gly Leu Gln Thr Phe Met Ile Ser Trp Arg
                245                 250                 255

Asn Pro Asp Val Arg His Arg Glu Trp Gly Leu Ser Thr Tyr Val Glu
            260                 265                 270

Ala Val Glu Glu Ala Met Asn Val Cys Arg Ala Ile Thr Gly Ala Arg
        275                 280                 285

Glu Val Asn Leu Met Gly Ala Cys Ala Gly Gly Leu Thr Ile Ala Ala
    290                 295                 300

Leu Gln Gly His Leu Gln Ala Lys Arg Gln Leu Arg Arg Val Ser Ser
305                 310                 315                 320

Ala Thr Tyr Leu Val Ser Leu Leu Asp Ser Gln Leu Asp Ser Pro Ala
                325                 330                 335

Ser Leu Phe Ala Asp Glu Gln Thr Leu Glu Ala Ala Lys Arg Arg Ser
            340                 345                 350

Tyr Gln Lys Gly Val Leu Asp Gly Arg Asp Met Ala Lys Val Phe Ala
        355                 360                 365

Trp Met Arg Pro Asn Asp Leu Ile Trp Ser Tyr Phe Val Asn Asn Tyr
    370                 375                 380

Leu Leu Gly Lys Glu Pro Pro Ala Phe Asp Ile Leu Tyr Trp Asn Asn
385                 390                 395                 400

Asp Ser Thr Arg Leu Pro Ala Ala Leu His Gly Asp Leu Leu Asp Phe
```

-continued

```
                405                 410                 415
Phe Lys His Asn Pro Leu Thr His Pro Gly Gly Leu Glu Val Cys Gly
            420                 425                 430

Thr Pro Ile Asp Leu Gln Lys Val Thr Val Asp Ser Phe Ser Val Ala
        435                 440                 445

Gly Ile Asn Asp His Ile Thr Pro Trp Asp Ala Val Tyr Arg Ser Thr
    450                 455                 460

Leu Leu Leu Gly Gly Glu Arg Arg Phe Val Leu Ser Asn Ser Gly His
465                 470                 475                 480

Val Gln Ser Ile Leu Asn Pro Pro Ser Asn Pro Lys Ala Asn Tyr Val
                485                 490                 495

Glu Asn Gly Lys Leu Ser Ser Asp Pro Arg Ala Trp Tyr Tyr Asp Gly
            500                 505                 510

Arg His Val Asp Gly Ser Trp Trp Thr Gln Trp Leu Ser Trp Val Gln
        515                 520                 525

Glu Arg Ser Gly Ala Gln Lys Glu Thr His Met Ala Leu Gly Asn Gln
    530                 535                 540

Asn Tyr Pro Pro Met Glu Ala Ala Pro Gly Thr Tyr Val Arg Val Arg
545                 550                 555                 560
```

<210> SEQ ID NO 4
<211> LENGTH: 1683
<212> TYPE: DNA
<213> ORGANISM: Pseudomonas cichorii H45 ; FERM BP-7374

<400> SEQUENCE: 4

| | |
|---|---|
| atgcgcgaga aaccagcgag ggattcgtta ccgactcccg ccgcgttcat | 50 |
| caatgcacag agtgcgatta ccggcctgcg cggtcgggat ctgttatcga | 100 |
| ccctgcgcag tgtggccgcc catggcttgc gcaatccggt gcacagtgcc | 150 |
| cgacatgccc tcaaactcgg cggccagctt ggtcgtgtgc tgctgggtga | 200 |
| aaccctgcac ccgaccaacc cgcaggacac tcgcttcgcc gatccggcgt | 250 |
| ggagcctcaa cccgttttac cggcgcagcc tgcaggccta tctgagctgg | 300 |
| cagaagcagg tcaaaagctg gatcgacgag agcgacatga gcccggacga | 350 |
| ccgcgcccgc gcccacttcg cttccgcctt gctcaacgac gccgtatcgc | 400 |
| cctccaacac cctgctcaat ccattggcgg tcaaggagct cttcaattcc | 450 |
| ggtggtaaca gcctggtgcg tggcatcggc catctggtgg acgatctgct | 500 |
| gcacaacgat ggcttgcccc ggcaagtcac caagcaagcg ttcgaggtcg | 550 |
| gcaagacggt cgccaccacc accggtgccg tggtgtttcg caacgaactg | 600 |
| ctggagttga tccagtacaa gccgatgagc gaaaagcagt attccaagcc | 650 |
| cctgctggtg gtgccgccac aaatcaacaa gtactacatt ttcgacctga | 700 |
| gcccccacaa cagcttcgtc cagtacgcgc tgaaaaacgg cctgcagacc | 750 |
| ttcatgatca gctggcgcaa cccggatgtg cgtcaccgtg aatggggggct | 800 |
| ctcgacctac gtggaagccg tggaagaggc catgaatgtg tgccgggcga | 850 |
| tcaccggcgc acgcgaggtc aacctgatgg gcgcctgcgc cggcgggttg | 900 |
| accattgccg cgttgcaagg ccacttgcag gccaagcgga actgcgcag | 950 |
| ggtgtccagt gcgacttatc tggtgagcct gctcgacagc cagctggata | 1000 |
| gccccgcttc gctgttcgcc gacgagcaga ctctggaggc cgccaagcgc | 1050 |

```
cgctcctatc agaaaggtgt gctggacggc cgcgacatgg ccaaggtctt        1100
cgcctggatg cgccccaacg atttgatctg gagctacttc gtcaacaact        1150
acctgttggg caaggagccg ccggcgttcg acatcctcta ctggaacaac        1200
gacagcacgc gcctgccggc cgccctgcat ggcgacctgc tggacttctt        1250
caagcacaac ccgctgaccc acccgggcgg cctggaagtg tgtggcacgc        1300
cgatcgattt gcagaaggtc accgtcgaca gcttcagcgt cgccggcatc        1350
aacgatcaca tcacgccgtg ggatgcggtg tatcgctcga cgctgttgct        1400
cggtggcgag cggcgctttg tgctatccaa cagcggtcat gtgcagagca        1450
tcctcaaccc gccgagcaac ccgaaagcca actacgtcga aaacggcaaa        1500
ctgagcagcg accccgcgc ctggtactac gacggcagga atgtcgacgg         1550
cagttggtgg acccaatggc tgagctgggt tcaggaacgc tccggcgcac        1600
agaaggaaac ccacatggcg ctcggcaacc agaactatcc accgatggaa        1650
gctgcgcccg gtacctacgt acgtgtgcgc tga                          1683
```

<210> SEQ ID NO 5
<211> LENGTH: 20
<212> TYPE: DNA
<213> ORGANISM: Artificial Sequence
<220> FEATURE:
<223> OTHER INFORMATION: Primer for PCR multiplication

<400> SEQUENCE: 5
tgctggaact gatccagtac                                          20

<210> SEQ ID NO 6
<211> LENGTH: 23
<212> TYPE: DNA
<213> ORGANISM: Artificial Sequence
<220> FEATURE:
<223> OTHER INFORMATION: Primer for PCR multiplication

<400> SEQUENCE: 6
gggttgagga tgctctggat gtg                                      23

<210> SEQ ID NO 7
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 7
ctacaaagct tgacccggta ctcgtctcag                               30

<210> SEQ ID NO 8
<211> LENGTH: 28
<212> TYPE: DNA
<213> ORGANISM: Artificial Sequence
<220> FEATURE:
<223> OTHER INFORMATION: Primer for PCR multiplication

<400> SEQUENCE: 8
cgagcaagct tgctcctaca gtagggcg                                 28

<210> SEQ ID NO 9
<211> LENGTH: 29
<212> TYPE: DNA
<213> ORGANISM: Artificial Sequence -continued

```
<220> FEATURE:
<223> OTHER INFORMATION: Primer for PCR multiplication

<400> SEQUENCE: 9
gttttaagct tgaagacgaa ggagtgttg                                    29

<210> SEQ ID NO 10
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 10
atcgcaagct tactcgctcc taccgggtc                                    29
```